US010488347B2

(12) United States Patent
Terasawa et al.

(10) Patent No.: US 10,488,347 B2
(45) Date of Patent: Nov. 26, 2019

(54) DEFECT CLASSIFICATION METHOD, METHOD OF SORTING PHOTOMASK BLANKS, AND METHOD OF MANUFACTURING MASK BLANK (71) Applicant: Shin-Etsu Chemical Co., Ltd., Tokyo (JP)

(72) Inventors: Tsuneo Terasawa, Niigata (JP); Hiroshi Fukuda, Niigata (JP); Daisuke Iwai, Niigata (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 16/391,725

(22) Filed: Apr. 23, 2019

(65) Prior Publication Data
US 2019/0331608 A1 Oct. 31, 2019

(30) Foreign Application Priority Data
Apr. 25, 2018 (JP) .................................. 2018-083583

(51) Int. Cl.
*G01N 21/88* (2006.01)
*G01N 21/956* (2006.01)
(Continued)

(52) U.S. Cl.
CPC ..... *G01N 21/8851* (2013.01); *G01N 21/8806* (2013.01); *G01N 21/894* (2013.01);
(Continued)

(58) Field of Classification Search
CPC ............... G01N 21/88; G01N 21/8803; G01N 21/8806; G01N 21/8851; G01N 21/892;
(Continued)

(56) References Cited

U.S. PATENT DOCUMENTS 3,887,762 A * 6/1975 Uno ...................... G01N 21/956
348/126
5,808,735 A * 9/1998 Lee ..................... G01N 21/9501
250/559.42
(Continued)

FOREIGN PATENT DOCUMENTS

JP 2001027611 A 1/2001
JP 2003004654 A 1/2003
(Continued)

*Primary Examiner* — Gordon J Stock, Jr.
(74) *Attorney, Agent, or Firm* — Westerman, Hattori, Daniels & Adrian, LLP (57) ABSTRACT A defect classification method in accordance with the present invention uses two types of images output from the defect inspection device 150 (i.e., the first inspection image generated from a luminance signal sequentially output from a detector SE and the second inspection image generated from a difference of the signals from an adjacent portion in a region where the defect exists). The first inspection image includes information for discriminating unevenness of the defective shape. Also, while it is difficult to discriminate unevenness of the defective shape by the second inspection image, the second inspection image includes information on a luminance distribution emphasizing a defective section. The region of the defective section is extracted from the second inspection image to be applied to the first inspection image and thereby define an arithmetic processing area, and the image processing is performed within the arithmetic processing area to compute a feature amount.

9 Claims, 5 Drawing Sheets

US 10,488,347 B2

Page 2

(51) Int. Cl.
  *G03F 7/20* (2006.01)
  *G03F 1/84* (2012.01)
  *G01N 21/894* (2006.01)
  *G01N 21/892* (2006.01)

(52) U.S. Cl.
  CPC ..... *G01N 21/956* (2013.01); *G01N 21/95623* (2013.01); *G03F 1/84* (2013.01); *G03F 7/7065* (2013.01); *G01N 2021/8854* (2013.01); *G01N 2021/8887* (2013.01); *G01N 2021/8924* (2013.01); *G01N 2021/95676* (2013.01)

(58) Field of Classification Search
  CPC ............. G01N 21/894; G01N 21/9501; G01N 21/9503; G01N 21/9506; G01N 21/956; G01N 21/95607; G01N 21/95623; G01N 21/95684; G01N 21/95692; G01N 21/958; G01N 2021/8809; G01N 2021/8854; G01N 2021/8858; G01N 2021/8861; G01N 2021/8863; G01N 2021/8867; G01N 2021/887; G01N 2021/8874; G01N 2021/8877; G01N 2021/8887; G01N 2021/889; G01N 2021/8893; G01N 2021/8896; G01N 2021/8924; G01N 2021/8925; G01N 2021/9513; G01N 2021/95615; G01N 2021/95676; G03F 1/84; G03F 7/7065
  See application file for complete search history.

(56) References Cited

U.S. PATENT DOCUMENTS

| | | | | |
|---|---|---|---|---|
| 5,949,900 A | * | 9/1999 | Nakamura | G01R 31/311 348/126 |
| 6,246,787 B1 | * | 6/2001 | Hennessey | G01N 21/95607 250/559.45 |
| 7,274,813 B2 | * | 9/2007 | Maeda | G01N 21/95607 356/237.2 |
| 7,283,659 B1 | * | 10/2007 | Bakker | G06K 9/6254 382/144 |
| 7,421,110 B2 | * | 9/2008 | Nakano | G06T 7/001 382/144 |
| 7,436,993 B2 | * | 10/2008 | Onishi | G06T 7/0004 382/144 |
| 7,564,545 B2 | * | 7/2009 | Stokowski | G03F 7/705 356/237.5 |
| 7,706,598 B2 | * | 4/2010 | Shimura | G01N 21/8803 382/144 |
| 7,991,217 B2 | * | 8/2011 | Nakagaki | G06K 9/6256 382/144 |
| 8,045,145 B1 | * | 10/2011 | Bakker | G01N 21/95607 356/237.1 |
| 8,582,864 B2 | * | 11/2013 | Maeda | G06T 7/001 348/125 |
| 9,305,343 B2 | * | 4/2016 | Nakahira | G06T 7/0004 |
| 9,310,320 B2 | * | 4/2016 | Kurada | G06K 9/66 |
| 9,518,934 B2 | * | 12/2016 | Chen | G01N 21/9501 |
| 9,772,551 B2 | * | 9/2017 | Terasawa | G01N 21/956 |
| 9,829,442 B2 | * | 11/2017 | Terasawa | G01N 21/956 |
| 9,829,787 B2 | * | 11/2017 | Terasawa | G01B 11/24 |
| 10,054,554 B2 | * | 8/2018 | Kato | G01B 11/30 |
| 10,295,477 B2 | * | 5/2019 | Terasawa | G03F 1/84 |
| 10,395,358 B2 | * | 8/2019 | Brauer | G06T 7/0004 |
| 10,395,362 B2 | * | 8/2019 | Gupta | G01N 21/9501 |
| 2006/0280358 A1 | * | 12/2006 | Ishikawa | G01N 21/95607 382/149 |
| 2013/0077092 A1 | | 3/2013 | Sasazawa et al. | |
| 2017/0328842 A1 | * | 11/2017 | Otani | G01N 21/95607 |
| 2017/0330315 A1 | * | 11/2017 | Okuda | G01N 21/8851 |
| 2018/0130199 A1 | * | 5/2018 | Brauer | G01N 21/9501 |
| 2018/0293721 A1 | * | 10/2018 | Gupta | G06T 7/001 |
| 2019/0257767 A1 | * | 8/2019 | Shaubi | G01N 21/9501 |

FOREIGN PATENT DOCUMENTS

| JP | 2013072788 A | 4/2013 |
| JP | 2017215277 A | 12/2017 |

* cited by examiner

DEFECT CLASSIFICATION METHOD, METHOD OF SORTING PHOTOMASK BLANKS, AND METHOD OF MANUFACTURING MASK BLANK

BACKGROUND OF THE INVENTION

Field of the Invention

The present invention relates to technologies associated with evaluation of defects in a photomask blanks used in manufacturing a photomask (transfer mask) which is used in manufacturing of a semiconductor device (semiconductor apparatus) or the like, and more particularly to defect evaluation technologies for evaluation of a photomask blank which is effective in determining a pit shape such as a pinhole existing in a thin film formed on the photomask blank. The present invention also relates to a method of sorting photomask blanks and a method of manufacturing a photomask blank using the above-mentioned technologies.

Description of the Related Art

Photolithography techniques are used in the manufacturing process of a semiconductor device (semiconductor apparatus) to irradiate a transfer mask with exposure light and transfer a circuit pattern formed on the photomask onto a semiconductor substrate (semiconductor wafer) by a reduction projection optical system. As unceasing efforts have been made to miniaturize a circuit pattern of semiconductor devices, a 193-nanometer (nm) wavelength with use of argon fluoride (ArF) excimer laser light now enjoys the mainstream status amongst the wavelengths of exposure light. Implementation of a multi-patterning process, which combines multiple rounds of exposure and processing processes, enables creation of a pattern that will eventually have a sufficiently small dimensions when compared with the exposure wavelength.

A pattern transfer mask is manufactured by forming a circuit pattern upon an optical film with a small thickness formed on a substrate (mask blank). Such an optical film is typically a film that contains a transition metal compound as its main component or a film that contains a silicon compound containing a transition metal as its main component. A film functioning as a light shielding film, a film functioning as a phase shift film, and the like are selected depending on the purposes. Further, a hard mask film which is a processing assistance film for the purpose of high-precision processing on the optical film may also be included.

If a defect is found in a transfer mask, which is used as an original for manufacturing of a semiconductor device having a certain circuit pattern, then the defect will be transferred to the circuit pattern. For this reason, the transfer mask is required to be defect-free, and this as a matter of fact requires that the photomask blank be defect-free. Under these circumstances, many studies have been made on techniques for detecting defects of a photomask or a photomask blank.

As a device for detecting a defect of a photomask blank, a glass substrate, etc., an inspection device is known which irradiates a substrate with a laser beam, receives by a photodetector the scattered light from a defect on the surface of the substrate, and detects presence of the defect on the basis of an output signal that is output from the photodetector. For example, Japanese Patent Laid-Open No. 2001-27611 discloses scanning of a surface of a sample using multiple light beams to detect, by a photodetector, the reflected light which is reflected from the sample. Also, Japanese Patent Laid-Open No. 2003-4654 discloses a detection optical system in which scanning of a surface of a sample by an optical beam spot to detect information on the surface region of the sample by means of the reflected light from the sample's surface. In the optical system disclosed, a light shielding plate that blocks a half of the light flux in the direction corresponding to the scanning direction of the optical spot is arranged on the optical path so as to discriminate between a bump defect and a pit defect in accordance with the shape of the output signal that is output from a photodetector.

Further, it is also known to generate a two-dimensional image including a defect from information collected by a defect inspection apparatus and classify the defect through image processing. As an example of a defect classification method through image processing, Japanese Patent Laid-Open No. 2013-72788 may be mentioned, which discloses a method of classifying a defect from inspection images using a classifier which is constructed on the basis of rule-based machine learning. Further, Japanese Patent Laid-Open No. 2017-215277 may also be mentioned, which describes specific parameters such as average luminance and perimeter of a defective section as feature amounts computed for defect classification through machine learning.

In the meantime, the inventors have collected and examined inspection images of numerous defects using existing optical defect inspection devices and found that, given an inspection image in which a minute defect was detected, the change in the luminance caused by the defect decreases until it almost reaches the level of change in luminance caused by thermal noise and electrical noise of a light receiving element, which may make it difficult to recognize a defect through image processing. In particular, a processing assistance layer formed for the purpose of processing on the advanced mask for pattern transfer using argon fluoride (ArF) excimer laser light is extremely thin with a thickness of 10 nm or less. It has also been found, for this and other reasons, that this tendency becomes conspicuous if a pit defect with a size of 100 nm or less exists in the defect inspection on a hard mask thin film.

The results of the examinations by the inventors have revealed the likelihood of occurrence of a problem that, since a defect is detected on the basis of the change in the luminance of the output signal from a photodetector, presence of the luminance change caused by the above-mentioned noise makes it difficult to recognize the location of the defect, which obscures the computation of the feature amount serving as the basis for the defect classification. In view of such a circumstance, it is desirable to provide a technique that avoids luminance change due to noise in the image processing on inspection images and significantly improves the level of defect recognition.

The present invention has been made in view of the above-identified problem and an object of the present invention is to provide a technique for significantly improving the level of defect recognition in relation to defect evaluation techniques using an optical defect inspection device. The present invention can be appropriately used in particular as a defect evaluation technique for a photomask blank effective in determination of a pit shape such as a pinhole existing in a thin film formed on the photomask blank.

SUMMARY OF THE INVENTION

In order to solve the above-identified problem, a defect classification method according to the present invention is a method of classifying a defect, wherein a surface of a to-be-inspected substrate is recognized, the method including the steps of scanning the surface of the to-be-inspected substrate with inspection light by using a defect inspection device having a confocal optical system (S1), detecting reflected light from the to-be-inspected substrate in a two-dimensional manner (S2), performing signal processing in a two-dimensional manner on an output signal corresponding to the reflected light (S3) and thereby detecting a defect on the surface of the to-be-inspected substrate (S4), performing image processing on an image obtained by the signal processing in the two-dimensional manner and classifying the defect that has been detected (S5). The image processing includes a first substep of processing a first inspection image and a second inspection image generated when a defect which is already classified is inspected by the defect inspection device to configure a classification criterion for classifying the defect through machine learning using a predefined parameter as a feature amount and a second substep of computing a feature amount from a first inspection image and a second inspection image obtained from the to-be-inspected substrate using the defect inspection device to classify the defect of the to-be-inspected substrate in accordance with the classification criterion. The computation of the feature amount of a defective section in the first substep and the second substep is performed by obtaining an approximate region where the defect exists in the second inspection image, applying the approximate region to the first inspection image, and limiting a region of image processing to compute a feature amount of a defective section.

According to an aspect, the first inspection image is a two-dimensional image of a region including a defect, generated by two-dimensionally arranging pieces of optical information obtained as reflected light when the substrate is scanned with the inspection light. The second inspection image is a two-dimensional image generated by performing delay of the optical information and subtracting the delayed optical information from the optical information applied to the first inspection image.

Also, according to an aspect, the first inspection image is generated from a luminance signal sequentially output from a detector provided in the defect inspection device, and the second inspection image is generated from a difference of signals from adjacent positions at certain intervals in a region where the defect exists.

For example, the inspection light is a light beam having a wavelength of 210 to 550 nm.

Also, according to an aspect, a spatial filter that blocks part of reflected light is provided on an optical path of a converging optical system when reflected light from a substrate is collected by a detector provided in the defect inspection device so as to collect the reflected light through the spatial filter.

Also, according to an aspect, the spatial filter converts a signal of a defect existing region sequentially output from the detector into a signal having an asymmetrical luminance profile.

Further, according to an aspect, the to-be-inspected substrate is a photomask blank including at least one layer of thin film having a thickness of 10 nm or less, and the classified defect is a pit defect or a pinhole defect of the thin film.

A method of sorting photomask blanks according to the present invention sorts out a photomask blank containing no pit defect by the above-described defect classification method.

Also, a method of manufacturing a photomask blank according to the present invention includes the steps of forming on a substrate at least one layer of thin film and a hard mask film which is a processing assistance layer for the thin film; and evaluating unevenness of a defect existing in the thin film or the hard mask film by the above-described defect classification method.

According to the present invention, even in a case where an inspection image collected using an optical defect inspection method is a low-contrast image, the location of the defect can be strictly recognized and the feature amount can be computed without influence of a noise component, so that it is made possible to implement image classification using machine learning with high reliability. As a result, it is made possible to classify a defect of a photomask blank regardless of a minute shape.

Also, implementation of the defect classification method according to the present invention achieves prevention of a bump defect from being falsely classified as a pit defect. As a result, a defect of a photomask blank leading to occurrence of a pit defect which is regarded as a critical defect of a photomask can be reliably detected. Consequently, it is made possible to ensure reduction in the costs associated with the manufacturing process of a photomask blank and a photomask and increase in the manufacturing yield thereof.

BRIEF DESCRIPTION OF THE DRAWINGS

FIGS. 1(A) to 1(C) are diagrams illustrating a typical example of a defect of a photomask blank, where

FIGS. 3(A) to 3(C) are diagrams illustrating operation of a feature amount computation unit 154 that computes a feature amount of a defect, where

FIGS. 6(A) and 6(B) are diagrams illustrating an example of a state of a defect that has been detected, where

DETAILED DESCRIPTION OF THE PREFERRED EMBODIMENTS

A defect classification method according to the present invention will be described hereinbelow with reference to the drawings.

A photomask blank is used in manufacturing of a photomask and includes an optical thin film formed on a substrate. If a defect such as a pinhole exists in this optical thin film, the defect causes a defect in a mask pattern on the photomask.

Figure 1A:
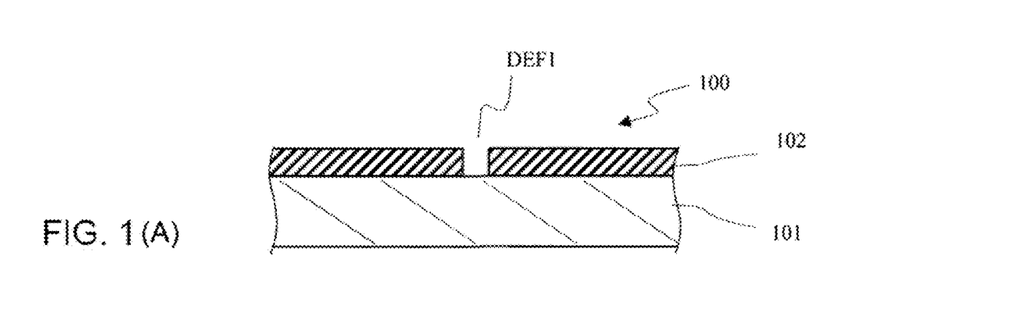
FIG. 1(A) is a diagram illustrating a state where a pinhole defect (DEF1) exists in an optical thin film provided on a transparent substrate.
Figure 1B:
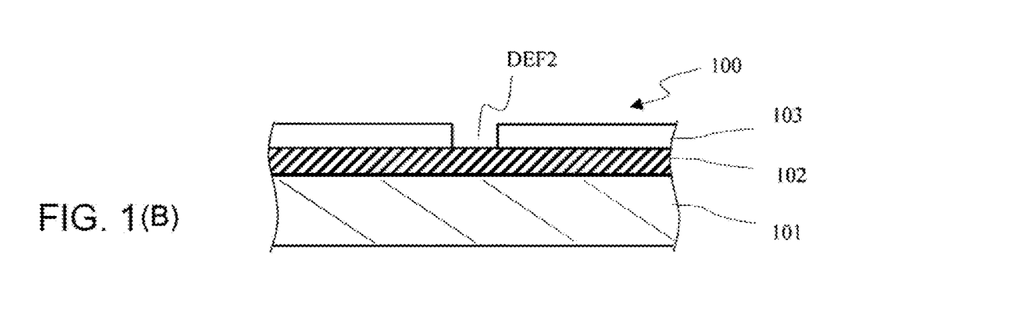
FIG. 1(B) is a diagram illustrating a state where a pinhole defect (DEF2) exists in a processing assistance thin film provided on an optical thin film on the transparent substrate.
Figure 1C:
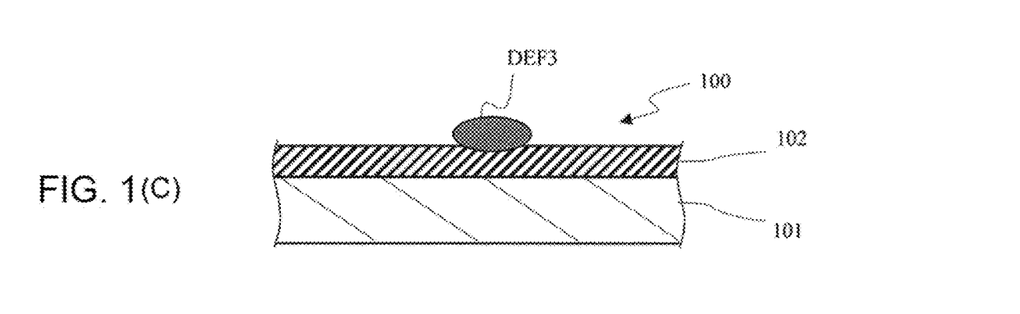
FIG. 1(C) is a diagram illustrating a state where a bump defect (DEF3) exists on an optical thin film provided on a photomask blank.

FIGS. 1(A) to 1(C) are diagrams that illustrates a typical example of a defect of a photomask blank. FIG. 1(A) is a diagram that illustrates a photomask blank 100 having an optical thin film 102 formed on a transparent substrate 101 and functioning as a light shielding film or a phase shift film for a halftone phase shift mask. A pit shaped pinhole defect (DEF1) exists in the optical thin film 102.

Also, FIG. 1(B) is a diagram that illustrates the photomask blank 100, where the optical thin film 102 that functions as a light shielding film or a phase shift film for the halftone phase shift mask and a processing assistance thin film 103 for performing high-precision processing on the optical thin film 102 are formed on the transparent substrate 101. A pit shaped pinhole defect (DEF2) exists in the processing assistance thin film 103.

Further, FIG. 1(C) is a diagram that depicts a state where a bump defect (DEF3) exists on the optical thin film 102 provided on the photomask blank 100.

Each of these defects (DEF1 to DEF3) may be the cause of occurrence of a defect at the time of manufacturing of a photomask. If a defect exists in a photomask, the defect becomes the cause of the pattern transfer error occurring in the exposure process. Therefore, it is necessary to detect a defect existing in a photomask blank at the stage prior to processing the photomask blank into a photomask, eliminate the photomask blank having the defect, and, if possible, perform correction of the defect.

In the meantime, a defect with the same material as optical thin film 102 and a defect as an attached foreign matter such as a particle may be mentioned as the bump defect (DEF3) as illustrated in FIG. 1(C). Even when a photomask is manufactured from a photomask blank in which such a bump defect exists using a conventional manufacturing process, it does not always follow that a pit effect is created which is regarded as a critical defect in a photomask.

Also, if a foreign matter defect attached on the surface can be removed by cleaning, then all that should be done to remove it prior to manufacturing of the photomask is to actually perform the cleaning, so that the presence of the foreign matter defect will not constitute a critical defect.

On the other hand, the pit defects (DEF1 and DEF2) as illustrated in FIG. 1(A) and FIG. 1(B) cause pit defects regarded as critical defects of a photomask and cannot be removed by cleaning, so that they are critical as long as they are defects found in a photomask blank.

Thus, a defect existing in a photomask blank may be critical or may not be critical depending on its shape. Accordingly, of importance in this respect is to determine the shape of the defect existing on the surface of the photomask blank, i.e., to determine whether or not the defect is pit or bump.

Figure 2:
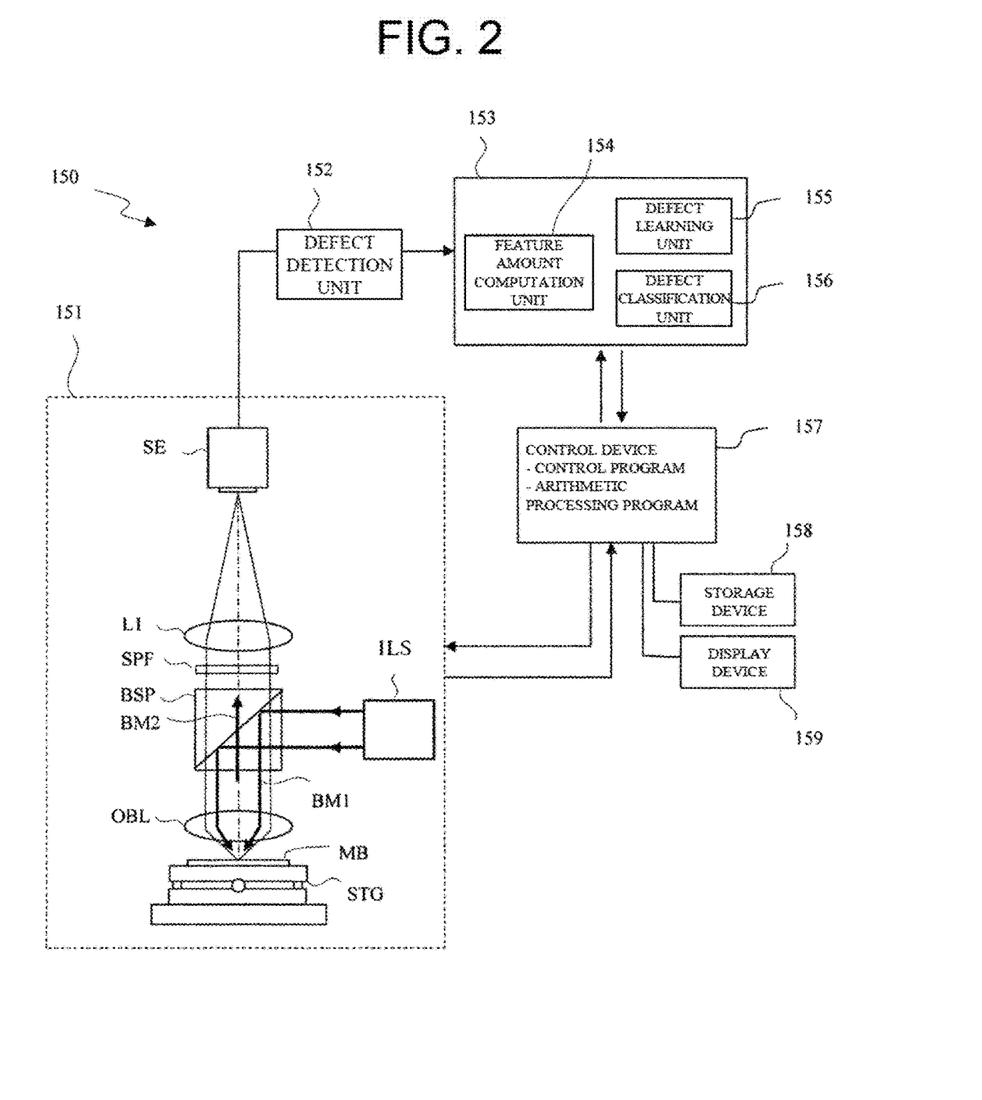
FIG. 2 is a block diagram conceptually illustrating a configuration of an inspection device appropriately used in determining a shape (either pit or bump) of a defect in a surface of a photomask blank.

FIG. 2 is a block diagram that conceptually describes an example of a configuration of an inspection device that is suitably used in determining the shape (pit or bump) of the defect on the surface of the photomask blank.

The defect inspection device 150 includes, as its constituent components, an inspection optical system 151, a defect detection unit 152, an image processing unit 153, a control device 157, a storage device 158, and a display device 159.

The inspection optical system 151 adopts a confocal optical system as its basic configuration and includes a light source ILS adapted to emit inspection light, a beam splitter BSP, an objective lens OBL, a stage STG on which the photomask blank MB can be placed and moved, and an image detector SE.

The light source ILS is configured such that it is capable of emitting a light beam having a wavelength in the order of 210 nanometers (nm) to 550 nm. The inspection light beam BM1 that has been emitted from the light source ILS is redirected by a beam splitter BSP so that a predetermined region of the photomask blank MB is irradiated with the inspection light beam BM1 via the objective lens OBL. The light beam BM2 that has been reflected by the surface of the photomask blank MB is collected by the objective lens OBL; passes through the beam splitter BSP, a spatial filter SPF that blocks part of the light, and the lens L1; and reaches the light receiving surface of the image detector SE.

At this point, the position of the image detector SE is adjusted such that the light receiving surface of the image detector SE is placed in a conjugate position with the surface of the mask blank MB. The inspection light beam BM1 with which the surface of the photomask blank MB is irradiated is scanned by a not-shown scanning unit and the image detector SE that receives the reflected light beam BM2 outputs a sequential luminance signal in response to the scanning to the defect detection unit 152.

It should be noted that scanning with the inspection light on the surface of the to-be-inspected substrate is carried out in a two-dimensional manner, for example, by scanning with the inspection light in an X direction and moving the stage in a Y direction orthogonal to the X direction.

At the time of the defect classification, in response to the scanning by the inspection light beam BM1, on the basis of the signal sequentially output from the image detector SE, the two-dimensional image of the region including the defect is generated, but in the present invention, defect detection by the defect detection unit 152 is carried out in advance prior to the generation of the two-dimensional image.

At the time of the defect detection by this defect detection unit 152, the spatial filter SPF that blocks part of the reflected light beam BM2 is provided on an optical path of the converging optical system collecting the reflected light beam BM2 from the substrate (photomask blank MB) and thereby the signal (defective section signal) of the area where the defect exists which is sequentially output from the image detector SE in response to the scanning by the inspection light beam BM1 is made to have an asymmetrical luminance profile. Simultaneously with the a symmetrization of the luminance profile, the difference between delayed signal obtained by delaying the above-described defective section signal by a predetermined time and non-delayed signal sequentially output from the image detector SE is obtained This difference is, specifically, the difference of signals from the adjacent positions at certain intervals in the region where the defect exists. Thereby the change in luminance (contrast difference) of the defective section is emphasized, and the defect is detected by applying a threshold to the emphasized signal.

Thus, the defect detection unit 152 obtains a difference between a delayed signal and a non-delayed signal of the luminance signal sequentially output from the image detector SE in response to the above-described scanning with the inspection light beam BM1, applies a threshold to the signal in which the change in luminance of the defective section is emphasized to detect the defect, and sends defect position information, a first inspection image generated from the luminance signal sequentially output from the detector SE, and a second inspection image generated from the above-described difference signal to the image processing unit 153.

The image processing unit 153 includes a feature amount computation unit 154, a defect learning unit 155, and a defect classification unit 156. The feature amount computation unit 154 is configured to perform computation of a feature amount of the defect by performing the image processing operation thereon and classification of the defect by the defect classification unit 156 is performed on the basis of the defect feature amount. Also, the results are recorded as defect information in the defect learning unit 155 and also stored in the storage device 158 which will be described later.

The control device 157 stores a control program and various image calculation programs. The control device 157 is connected to each of the inspection optical system 151, the image processing unit 153, the storage device 158, and the display device 159 and configured to control the entire inspection device 150.

The defect classification method in accordance with the present invention uses the above-described two types of images output from the defect inspection device 150 (first inspection image generated from the luminance signal sequentially output from the detector SE and the second inspection image generated from the difference of the signals from the adjacent positions at certain intervals in the region where the defect exists). The first inspection image includes information for discriminating between bump and pit defective shape. Also, the second inspection image cannot be used to discriminate the defective shape but has the information on the luminance distribution for emphasizing the defective section.

In view of this, first, the arithmetic processing area is narrowed down by the second inspection image having the information on the luminance distribution emphasizing the defective section. Subsequently, the feature amount of the defect in the region corresponding to the above-described narrowed-down arithmetic processing area of the first inspection image including the information for discriminating between bump and pit defective shape is calculated. In the present invention, by virtue of such a procedure, degradation in the reliability of the feature amount computation is prevented.

Figure 3A:
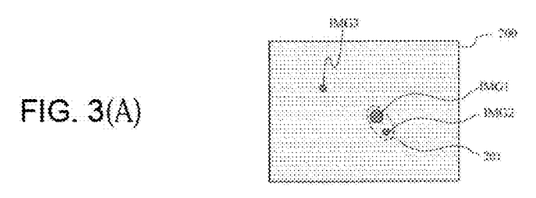
FIG. 3(A) is a diagram illustrating a first two-dimensional inspection image.
Figure 3B:
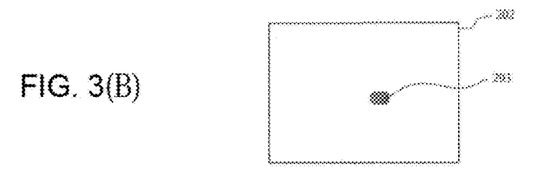
FIG. 3(B) is a diagram illustrating a second two-dimensional inspection image.
Figure 3C:
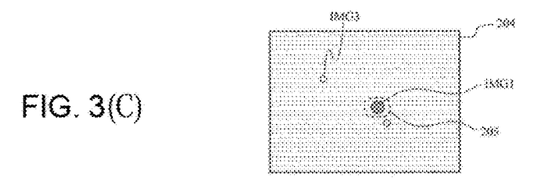
FIG. 3(C) is a diagram illustrating the first two-dimensional inspection image with an arithmetic processing area identified.

FIGS. 3(A) to 3(C) are diagrams that illustrates the operation of the feature amount computation unit 154 that computes the feature amount of the defect, where FIG. 3(A) is a diagram that illustrates the first (two-dimensional) inspection image, FIG. 3(B) is a diagram that illustrates the second (two-dimensional) inspection image, and FIG. 3(C) is a diagram that illustrates the first (two-dimensional) inspection image with the arithmetic processing area identified.

The element indicated by the reference sign 200 in FIG. 3(A) is a schematic diagram of the first (two-dimensional) inspection image 200 generated from the luminance signal sequentially output from the image detector SE in response to the scanning by the inspection light, where the horizontal striped pattern indicates the scanning lines.

The first inspection image includes change in luminance IMG1 caused by the defect and also includes luminance changes IMG2 and IMG3 caused by noise, etc.

In a conventional method, if these luminance changes are substantially equal to each other, then, for example, the region indicated by a contour line 201 is recognized as the defective section to compute, as the feature amounts, the size of the defect and the average luminance of the defect. However, according to such a scheme, since the luminance change IMG2 caused by noise, etc. is included in the contour line 201 in addition to the luminance change IMG1 caused by the defect, it will not be possible to implement accurate defect evaluation.

In view of this, according to the present invention, by using the above-described second inspection image, the arithmetic processing area for which the feature amount of the defect is computed is correctly narrowed down.

Specifically, in order to emphasize the presence of the defect, as illustrated in FIG. 3(B), the luminance change area 203 is extracted, which is included in the second inspection image 202 generated from the difference of the signals from the adjacent positions at certain intervals in the region where the defect exists.

Since the second inspection image 202 is basically a difference signal, the striped pattern of scanning lines appearing in the first inspection image is not likely to be created. As the method for obtaining the luminance change area 203, for example, a method may be mentioned which compares the region exhibiting luminance change emphatically rendered in the defective section relative to the luminance of the region where no defect exists with a predetermined threshold to obtain the region of emphasized luminance change as the number of pixel and subsequently perform, in combination, the dilation and erosion in signal processing by the a predetermined number of times as employed in conventional image processing. It is also possible to define a rectangular area circumscribing the obtained area as the luminance change area 203.

This luminance change area is extracted as the number of the pixel of the two-dimensional image and this number is made to correspond again to the pixel number of the first inspection image to define the area, and as in the third inspection image 204 illustrated in FIG. 3(C), the arithmetic processing area 205 for computation of the feature amount is specified. It should be noted that the third inspection image 204 illustrated in FIG. 3(C) is basically the same as the first inspection image 200 illustrated in FIG. 3(A), but differs therefrom in that the area 205 for computation of the feature amount is additionally indicated.

After the arithmetic processing area 205 has been specified, feature amounts specified in advance such as the average luminance of the defective section, the area of the defective section, and the luminance gradient are computed from the information on the change in luminance of the defective section within the area.

By the above-described method, the maximum value and the minimum value of the pixel intensity caused by a noise component in a location away from the defective section can be prevented from being selected.

Referring again to FIG. 2, the image processing unit 153 will be described.

Prior to the defect classification, first, with regard to the defects whose classification is known, their first inspection image and second inspection image are read, the above-described feature amount is computed, and learning by the defect learning unit 155 is carried out. The classification as used herein refers to classification regarding, for example, unevenness (pit shape or bump shape) of defects, whether or not a defect has a scratch-like shape, etc. A greater number of defects to be learned are more preferable and at least 20 defects are desirable. By learning of these inspection images, the classification criterion is configured.

Multiple classification criteria should be preferably configured in accordance with the structures of the to-be-inspected substrates such as a substrate having a photomask blank to be subjected to the defect inspection and various film structures, a transparent substrate, and the like.

Next, the new inspection images of the defects of the to-be-inspected substrate whose defects should be classified are read. In the same manner as in machine learning, the feature amount is computed from the first two-dimensional inspection image and the second two-dimensional inspection image and, by the defect classification unit 156, the defects are classified in accordance with the previously configured classification criterion.

These classification results are stored along with the information on the defect inspection in the storage device 158 and are allowed to be readily confirmed by an operator by displaying the two-dimensional inspection image and the classification results on the display device 159.

Figure 4:
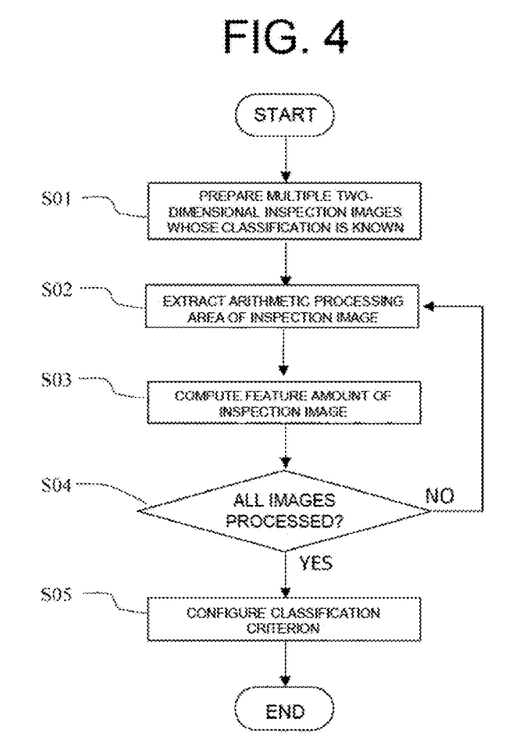
FIG. 4 is a flow diagram of configuring a classification criterion through machine learning of inspection images of defects.

FIG. 4 is a flow diagram of the process of configuring a classification criterion through machine learning of the inspection images of defects.

First, with regard to numerous defects whose classification is known, their first two-dimensional inspection images and second inspection images are prepared (step S01). Next, in the step S02, a region of a defective section is extracted from the second inspection image with one defect to be subjected to the first inspection image and define the arithmetic processing area. Subsequently, image processing is performed in the arithmetic processing area of the first inspection image to compute the feature amount (step S03). Whether or not all the two-dimensional inspection images that were prepared have been processed is determined in the determination step S04. If all of the two-dimensional inspection images have not yet been processed, then the process goes back to the step S02 to repeat the processing on the remaining image(s). When the processing has been completed for all of the inspection images, then a classification criterion is configured on the basis of the computed feature amount and known classification information (step S05).

Figure 5:
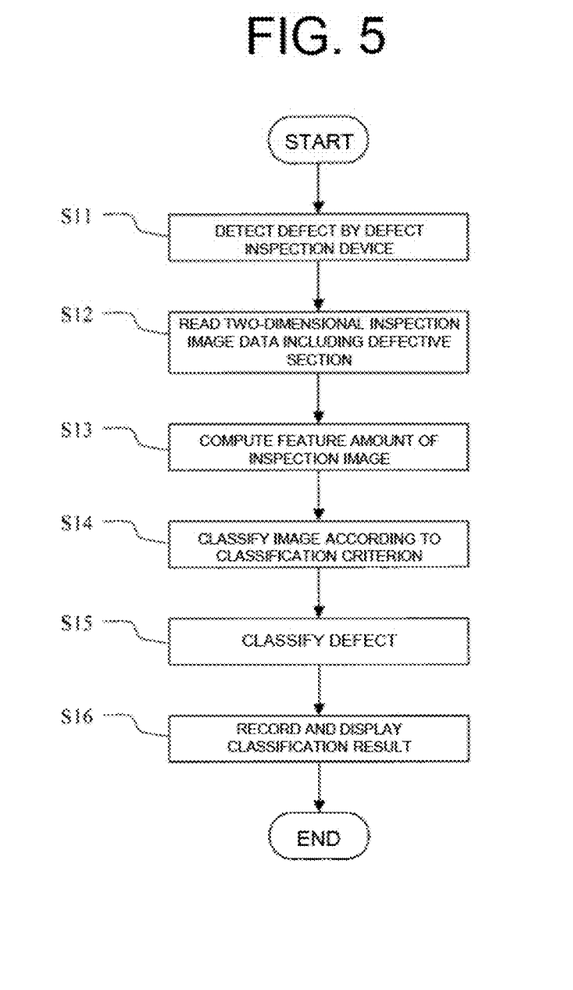
FIG. 5 is a flow diagram of classifying a defect of a to-be-inspected substrate in accordance with the classification criterion.

FIG. 5 is a flow diagram of classification performed on defects of a to-be-inspected substrate in accordance with the classification criterion.

First, the to-be-inspected substrate is inspected by the inspection device and defect detection is performed by a known inspection method (step S11). Next, data of the first inspection image and the second inspection image including the defective section and being output from the inspection device is read (step S12). The region of the defective section is extracted from the second inspection image to be subjected to the first inspection image and the arithmetic processing area is defined, and image processing is performed in the arithmetic processing area to compute the feature amount (step S13). Next, the image is classified in accordance with the classification criterion that has been configured (step S14). The defect is classified based on the result of the image classification (step S15), the classification result is recorded, and the classification result is displayed as needed on the display device (step S16).

It should be noted that the classification criterion may be reconfigured using the results of classification as new data for learning.

Thus, the image arithmetic processing area obtained by the second inspection image is applied to the first inspection image so as to compute the feature amount of the defect, the inspection images of the defects of the to-be-inspected substrates are classified in accordance with the machine learning of the inspection image whose classification is known and the classification criterion configured by the machine learning, and thus evenness, etc. of the defects can be evaluated with a high reliability and accurate defect classification can be implemented.

Also, implementation of the defect classification method of the present invention in a manufacturing process of a photomask blank makes it possible to extract with high reliability a pit defect, in particular a photomask blank having a pinhole defect, and sort out only the photomask blanks that do not contain any pinhole defect.

Further, it is made possible to effectively exclude a photomask blank having a defect that causes occurrence of a pit defect constituting a critical defect for a photomask, which contributes to increase in the manufacturing yield of photomask blanks.

Whilst the present invention will be specifically described below with reference to examples thereof, the present invention is not limited to the following examples.

Example 1

The photomask blank used in this example is a photomask blank for producing a halftone phase shift mask where ArF excimer laser with a 193-nm wavelength is used as the exposure light. A quartz substrate (size: about 152 mm×152 mm; thickness: 6.35 mm) was prepared as a substrate transparent to the exposure light, and a halftone phase shift film including molybdenum (Mo) and silicon (Si) as its main components was formed on the prepared substrate, and further a light shielding film including chromium (Cr) as its main component was formed on the former film. In total, 60 photomask blanks were produced in this manner.

Next, for the purpose of image data collection for machine learning, defect inspection was performed on the light shielding film of the photomask blank. The defect inspection device M6640S (manufactured by Lasertec Corporation) which has a confocal optical system and includes a spatial filter blocking part of the inspection light was used in this defect inspection.

As a result, a total of 62 defects were detected from 40 photomask blanks out of the 60 photomask blanks. The shapes of these defects were measured using an atomic force microscope (AFM) to find 48 pit defects and 14 bump defects.

Figure 6A:
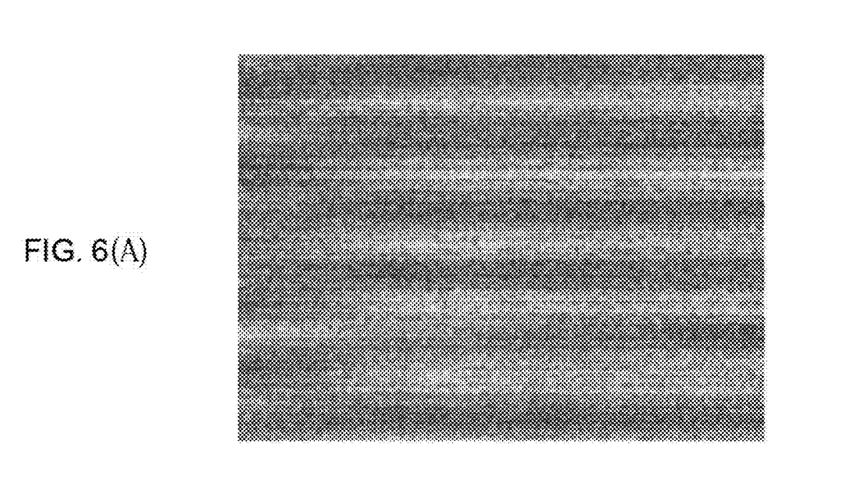
FIG. 6(A) is a first inspection image of a pit defect detected by the defect inspection device and FIG. 6(B) is a diagram illustrating a state of luminance distribution across a defective section in the first inspection image.
Figure 6B:
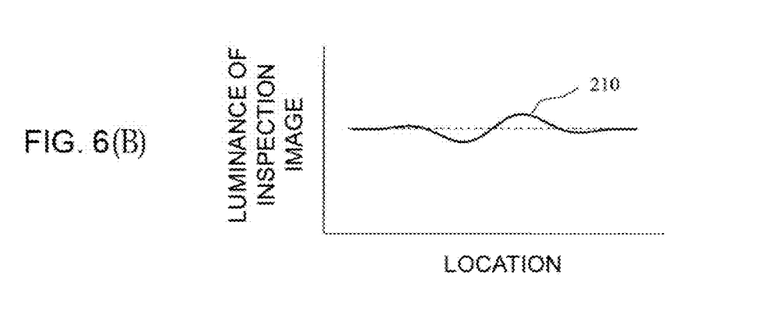

FIGS. 6(A) and 6(B) are diagrams that illustrates an example of the state of the defect that was detected, where FIG. 6(A) is a first inspection image of the pit defect that was detected by the defect inspection device, and FIG. 6(B) is a diagram that illustrates a cross-sectional profile of the luminance distribution across the defective section in the first inspection image.

The first inspection image of FIG. 6(A) is an image generated by scanning with the inspection light, so that a striped pattern extending in the scanning direction exists in an overlapping manner. The width of the pit defect observed in this image is wide in the order of about 200 nm, but the depth is shallow in the order of 5 nm or less, so that the contrast of the inspection image is low.

As described above, since the defect inspection device includes the spatial filter, according to the simulation, the luminance distribution across the defective section in the first inspection image will be as described in the schematic diagram of the FIG. 6(B), where the left side and the right side will be the dark part and the bright part, respectively.

However, in the case of an image where the contrast of the defective section is low as illustrated in FIG. 6(A), it becomes difficult to discriminate between luminance change caused by a defect and luminance change caused by noise, etc. other than the defect, which in turn makes it difficult to extract a portion that includes the luminance distribution for computation of the feature amount of the defective section. In view of this, in this example, at the time of the defect detection, the second inspection image is used which is generated from a signal generated by the defect inspection device and emphasizing the defective section.

Figure 7:
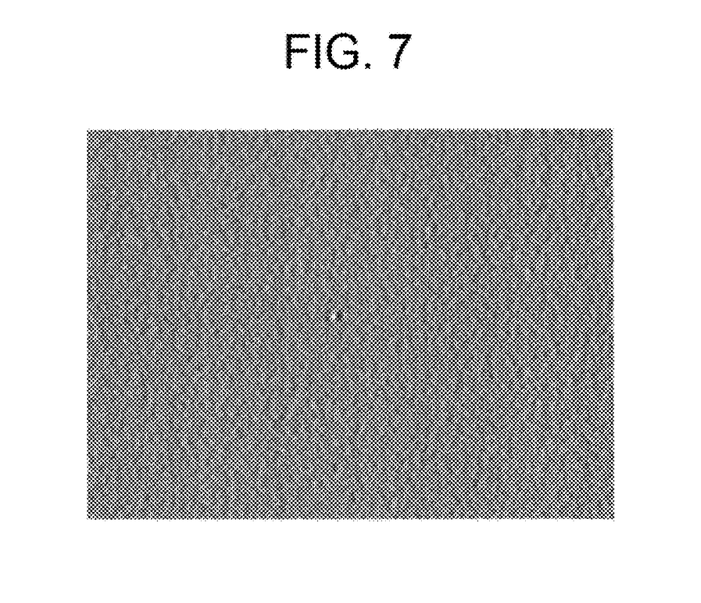
FIG. 7 is a second inspection image corresponding to the inspection image illustrated in FIG. 6(A).

FIG. 7 illustrates the second inspection image which corresponds to the first inspection image of FIG. 6(A). Basically, since the difference is obtained between a delayed signal and a signal that is not delayed, the defective section is emphasized and the noise signal components other than the defect are reduced.

As can be appreciated from FIG. 7, since the region of the defective section is clearly recognized, the defective section region was also recognized as the defective section region in the first inspection image illustrated in FIG. 6(A) as well, and thus the region for computation of the feature amount of the defective section was confined. Specifically, the pre-defined threshold was applied to the second inspection image, the region of the bright section and dark section due to a defect was obtained as the number of the pixel, and then the dilation operation with a predetermined number of times was performed on both of the regions to obtain a region which is obtained by interconnecting these regions, and then the rectangular region circumscribing the former region is defined as the feature amount computation region.

With regard to each of a total of 62 inspection images in which classification of the pit or bump shape of the defect is known and which were prepared for machine learning, by the same manner, the feature amount computation region was obtained and the feature amount of the defect was computed. From the feature amount and the unevenness classification information, the classification criterion was configured which classifies the defects into the defects having a pit shape and defects having a bump shape, and the defect classification was performed on the to-be-inspected substrate in accordance with the classification criterion.

The structure of the to-be-inspected substrate is the same as that of the photomask blank prepared for the above-described machine learning, and is a photomask blank obtained by forming a halftone phase shift film including molybdenum (Mo) and silicon (Si) as its main components on the quartz substrate and forming a light shielding film including chromium (Cr) as its main component on the former film.

While a shallow defect was found among the defects that have been detected by the inspection device, extraction of the feature amount computation region using the above-described second inspection image and computation of the feature amount from the first inspection image were performed, and, the classification was performed on the defects to determine whether their shape is pit or bump in accordance with the classification criterion. After the defect classification, for the purpose of confirmation, the classification result was compared with the AFM shape measurement result of the defect and it was found that the accuracy of the classification was 98%, which is a favorable value. It should be noted that the accuracy in the case where the defect classification is made in accordance with a conventional scheme is roughly in the order of 80% and those having a small size are falsely detected in most cases.

It should be noted that a large pinhole defect exhibited a high contrast of the first inspection image and was easily classified as a pit defect. Also, by application of the defect classification method according to the present invention, a photomask blank that includes the pinhole defect which is a critical defect was able to be excluded and a photomask blank that did not include any defect was allowed to be provided.

INDUSTRIAL APPLICABILITY

The present invention provides techniques for significantly improving the level of defect recognition in the defect evaluation technology using an optical defect inspection device. The present invention can in particular be appropriately used as defect evaluation technology for photomask blanks effective in determination of the pit shape such as a pinhole existing in a thin film formed on a photomask blank.

REFERENCE SIGNS LIST

100: photomask blank
101: transparent substrate
102: optical thin film
103: hard mask film
150: defect inspection device
151: inspection optical system
152: defect detection unit
153: image processing unit
154: feature amount computation unit
155: defect learning unit
156: defect classification unit
157: control device
158: storage device
159: display device
200: first (two-dimensional) inspection image
201: contour line
202: second (two-dimensional) inspection image
203: luminance change area
204: third (two-dimensional) inspection image
205: arithmetic processing area for feature amount computation
BM1: inspection light
BM2: reflected light
BSP: beam splitter
DEF1: pinhole defect
DEF2: pinhole defect
DEF3: bump defect
ILS: light source
IMG1: luminance change section caused by a defect
IMG2: luminance change section caused by noise
IMG3: luminance change section caused by noise
L1: lens
MB: photomask blank
OBL: objective lens
SE: optical detector
STG: stage

What is claimed is:
1. A method of classifying a defect recognized on a surface of a to-be-inspected substrate, the method comprising the steps of:
scanning the surface of the to-be-inspected substrate with inspection light by using a defect inspection device having a confocal optical system (S1);
detecting reflected light from the to-be-inspected substrate in a two-dimensional manner (S2);

performing signal processing in a two-dimensional manner on an output signal corresponding to the reflected light (S3) and thereby detecting the defect on the surface of the to-be-inspected substrate (S4);

performing image processing on an image obtained by the signal processing in the two-dimensional manner and classifying the defect that has been detected (S5), the image processing including:

a first substep of processing a first inspection image and a second inspection image generated when a defect on a substrate whose surface defect is classified is inspected by the defect inspection device to configure a classification criterion for classifying the defect through machine learning using a predefined parameter as a feature amount; and a second substep of computing a feature amount from a first inspection image and a second inspection image obtained from the to-be-inspected substrate using the defect inspection device to classify the defect of the to-be-inspected substrate in accordance with the classification criterion, wherein computation of the feature amount of a defective section in the first substep and the second substep is performed by obtaining an approximate region where the defect exists in the second inspection image, applying the approximate region to the first inspection image, and limiting a region of image processing to compute a feature amount of a defective section.

2. The defect classification method according to claim 1, wherein the first inspection image is a two-dimensional image of a region including a defect, generated by two-dimensionally arranging pieces of optical information obtained as reflected light when the substrate is scanned with the inspection light, and the second inspection image is a two-dimensional image generated by performing delay of the optical information and subtracting the delayed optical information from the optical information applied to the first inspection image.

3. The defect classification method according to claim 1, wherein the first inspection image is generated from a luminance signal sequentially output from a detector provided in the defect inspection device, and the second inspection image is generated from a difference of signals from adjacent positions at certain intervals in a region where the defect exists.

4. The defect classification method according to claim 1, wherein the inspection light is a light beam having a wavelength of 210 to 550 nm.

5. The defect classification method according to claim 1, wherein a spatial filter that blocks part of reflected light is provided on an optical path of a converging optical system when reflected light from a substrate is collected by a detector provided in the defect inspection device so as to collect the reflected light through the spatial filter.

6. The defect classification method according to claim 5, wherein the spatial filter converts a signal of a defect existing region sequentially output from the detector into a signal having an asymmetrical luminance profile.

7. The defect classification method according to claim 1, wherein the to-be-inspected substrate is a photomask blank including at least one layer of thin film having a thickness of 10 nm or less, and the classified defect is a pit defect or a pinhole defect of the thin film.

8. A method of sorting photomask blanks, the method comprising:
sorting out a photomask blank containing no pit defect by the defect classification method according to claim 1.

9. A method of manufacturing a photomask blank, the method comprising the steps of:
forming on a substrate at least one layer of thin film and a hard mask film which is a processing assistance layer for the thin film; and
evaluating unevenness of a defect existing in the thin film or the hard mask film by the defect classification method according to claim 1.

* * * * *